United States Patent
Andagar Ramakrishna et al.

(10) Patent No.: US 10,781,163 B2
(45) Date of Patent: Sep. 22, 2020

(54) PROCESS FOR PREPARATION OF O-DESMETHYLTRAMADOL AND SALTS THEREOF

(71) Applicant: R L FINECHEM PRIVATE LIMITED, Bangalore, Karnataka (IN)

(72) Inventors: Ramesha Andagar Ramakrishna, Bangalore (IN); Sidde Gowda, Bangalore (IN)

(73) Assignee: R L FINECHEM PRIVATE LIMITED, Bangalore, Karnataka (IN)

( * ) Notice: Subject to any disclaimer, the term of this patent is extended or adjusted under 35 U.S.C. 154(b) by 0 days.

(21) Appl. No.: 16/634,103

(22) PCT Filed: Nov. 8, 2017

(86) PCT No.: PCT/IB2017/056971
§ 371 (c)(1),
(2) Date: Jan. 24, 2020

(87) PCT Pub. No.: WO2019/053494
PCT Pub. Date: Mar. 21, 2019

(65) Prior Publication Data
US 2020/0231536 A1    Jul. 23, 2020

(30) Foreign Application Priority Data
Sep. 18, 2017   (IN) .............................. 201741033022

(51) Int. Cl.
| | | |
|---|---|---|
| *C07C 213/10* | (2006.01) |
| *C07C 213/04* | (2006.01) |
| *C07C 215/64* | (2006.01) |

(52) U.S. Cl.
CPC .......... *C07C 213/10* (2013.01); *C07C 213/04* (2013.01); *C07C 215/64* (2013.01); *C07C 2601/14* (2017.05); *C07C 2601/16* (2017.05)

(58) Field of Classification Search
CPC . C07C 213/10; C07C 213/04; C07C 2601/14; C07C 2601/16; C07C 215/64; C07C 255/59; C07C 217/52; C07C 217/74; A61P 25/04
See application file for complete search history.

(56) References Cited

U.S. PATENT DOCUMENTS

| | | | |
|---|---|---|---|
| 5,728,885 A | 3/1998 | Buschmann et al. |
| 5,801,201 A | 9/1998 | Graudums et al. |

FOREIGN PATENT DOCUMENTS

| | | |
|---|---|---|
| WO | 93/004675 A1 | 3/1993 |
| WO | 03/048113 A1 | 6/2003 |

OTHER PUBLICATIONS

Shao et al., "Derivatives of tramadol for increased duration of effect," Bioorganic & Medicinal Chemistry Letters, 2006, vol. 16, pp. 691-694.
Venkanna et al., "Synthesis of related substances of Tramadol hydrochloride, analgesic drug," Journal of Chemical and Pharmaceutical Research, 2012, vol. 4, No. 10, pp. 4506-4513.
Jun. 7, 2018 International Search Report issued in International Patent Application No. PCT/IB2017/056971.
Jun. 7, 2018 Written Opinion of the International Searching Authority issued in International Patent Application No. PCT/IB2017/056971.

*Primary Examiner* — Jafar F Parsa
(74) *Attorney, Agent, or Firm* — Oliff PLC

(57) ABSTRACT

A process of preparation of O-Desmethyl tramadol through potassium hydroxide mediated demethylation of Tramadol under phase transfer conditions.

11 Claims, 2 Drawing Sheets

PROCESS FOR PREPARATION OF O-DESMETHYLTRAMADOL AND SALTS THEREOF

FIELD OF INVENTION

The present invention relates to the field of synthetic chemistry. In particular to compound (1RS, 2RS)-2-[(Dimethylamino)methyl]-1-(3-hydroxy phenyl)cyclohexanol, commonly known as O-Desmethyl tramadol. The invention relates to the preparation of O-Desmethyl tramadol and its salts. The target compound is obtained in high yield and purity by aeco-friendly, economically viable and industrially scalable process.

BACKGROUND OF INVENTION

Pain management is a complex phenomenon due to multitudinous causes associated with it. Generally, pain gets subsided as the underlying pathology is managed with curative or palliative measures, most often with suitable drug compounds. Hence, there is a need for effective drugs preferably which doesn't have adverse side effects.

Tramadol hydrochloride is a well-known pain management drug, similar to a narcotic (opioid) pain management drug. Tramadol is prescribed for prolonged pain management, as it does not have adverse side effects associated with opioids. The structural formula of Tramadol (formula A) and its isomers are given in Formula (1A) and Formula (1B).

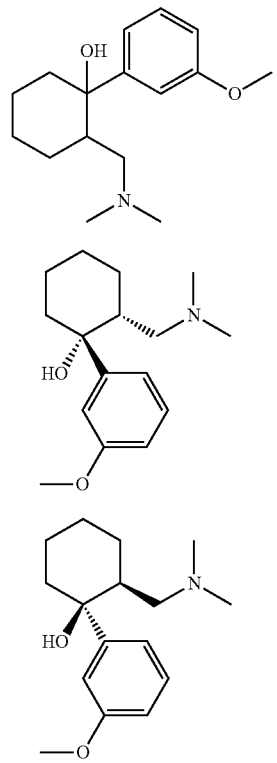

Formula 1

Formula 1A

Formula 1B

Tramadol is metabolized in the liver of human body, and its main metabolite is O-desmethyl tramadol (Formula II). The isomers of O-desmethyltramadol is represented formula IIA and IIB. This is known to be more potent and active than Tramadol. O-Desmethyl tramadol is potent μ opioid agonist as compared to tramadol. Additionally, it is a high affinity ligand of the δ- and κ-opioid receptors.

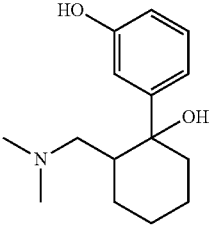

Formula II

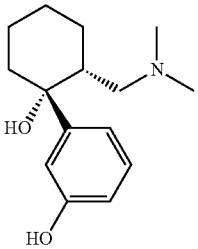

Formula IIA

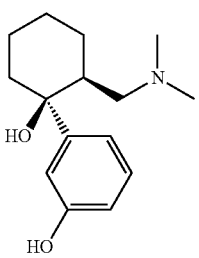

Formula IIB

There are various literature documents which informs about the synthesis of O-Desmethyl tramadol in several ways. Diisobutylaluminium hydride is used in a process filed under the patent document WO2003048113. Shao, Liming et al, in Bioorganic & Medicinal Chemistry, Letters, 16(3), 691-694; 2006 use Biphenyl phosphine and butyl lithium for the preparation of O-Desmethyl tramadol. Venkanna, G. et al disclose in Journal of Chemical and Pharmaceutical Research, 4(10), 4506-4513; 2012, that Boron tribromide can be used to bring about preparation of O-Desmethyl tramadol.

U.S. Pat. No. 5,801,201A discloses a process for the preparation O-Desmethyl tramadol. It employs chromatographic purification techniques, which is not economically feasible on a large-scale preparation of the product. CN1073085C discloses a process for preparing O-desmethyl tramadol enantiomers with L-(+)-tartaric acid. Variation in temperature controls in this process makes it highly strenuous, thus non-economical; further this process has low product recovery.

Thus most of the procedures involving preparation of Tramadol are tedious, involve hazardous reagents; hence not viable on industrial scale. Considering the importance of Tramadol as an analgesic in the medicinal field, it is important to develop economical and ecofriendly process to cater to the requirements. The present invention aims to provide a process that emphasizes on an efficient and eco-friendly process with high yield and highly pure form of product.

SUMMARY OF INVENTION

The invention relates to synthesis of O-Desmethyltramadol, by an industrially scalable process of demethylation of Tramadol which is mediated through potassium hydroxide in monoethylene glycol, under phase transfer conditions in high yield. The O-Desmethyltramadol synthesised by said process has a purity of more than 85-90% as measured by HPLC.

The present invention relates to a process for preparation of O-Desmethyl tramadol (formula (II)), comprising acts of

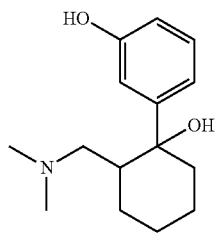

Formula II i) reacting trainadol of formula (I)

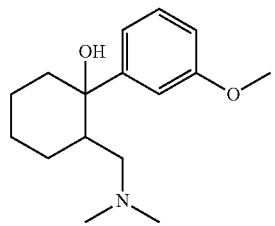

(Formula I)

with a potassium salt, in an organic solvent to obtain a mixture;
ii) heating the mixture;
iii) diluting the mixture with water to obtain an aqueous phase; and
iv) acidifying the aqueous phase with an acidic reagent and filtering to obtain compound of formula (II).

The present invention is also in relation to a process for obtaining salt of O-Desmethyl tramadol comprising acts of
a) reacting Tramadol of formula (I) with potassium salt in an organic solvent to obtain a mixture;

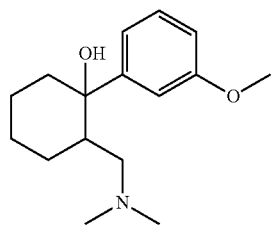

(Formula I)

b) heating the mixture;
c) diluting the mixture with water to obtain an aqueous phase;
d) acidifying the aqueous phase with an acidic reagent and filtering to obtain 0-Desmethyltramadol of formula (II); and
e) convertingthe O-Desmethyltramadol of formula (II) to salt of o-chlorobenzoic acid basifying with ammonia and treating with preferred acidic reagent to obtain salt of O-Desmethyltramadol.

BRIEF DESCRIPTION OF FIGURES

The features of the present invention can be understood in detail with the aid of appended figures. It is to be noted however, that the appended figures illustrate only typical embodiments of this invention and are therefore not to be considered limiting of its scope for the invention.

DETAILED DESCRIPTION OF INVENTION

Figure 1:
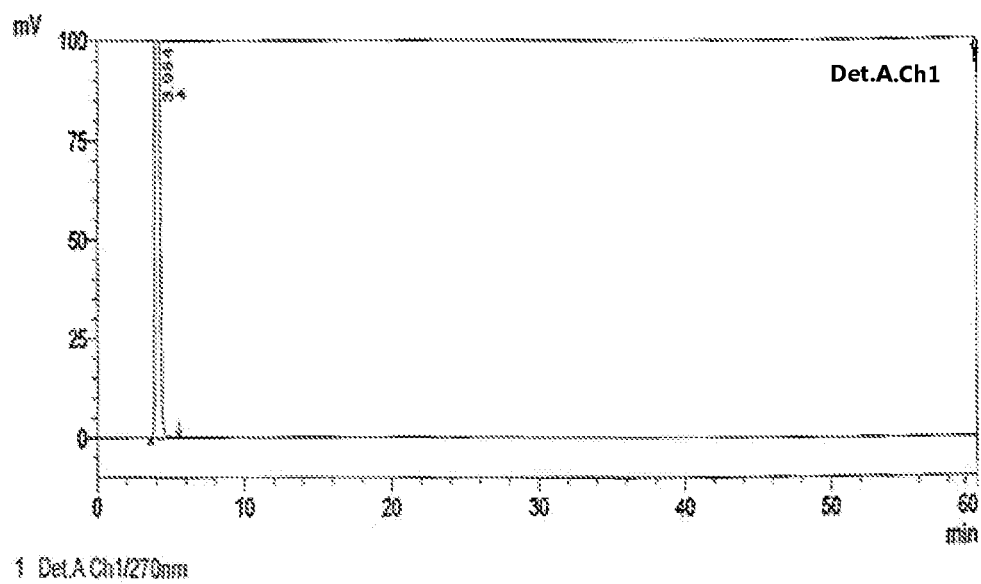
FIG. 1: HPLC diagram indicating the purity level of the 0-Desmethyl Tramadol (cis-isomer)

The foregoing description of the embodiments of the invention has been presented for the purpose of illustration. It is not intended to be exhaustive or to limit the invention to the precise form disclosed as many modifications and variations are possible in light of this disclosure for a person skilled in the art in view of the Figures, description and claims. It may further be noted that as used herein and in the appended claims, the singular "a" "an" and "the" include plural reference unless the context clearly dictates otherwise. Unless defined otherwise, all technical and scientific terms used herein have the same meanings as commonly understood by person skilled in the art.

The present invention relates to a process for preparation of 0-Desmethyl tramadol (formula (II)), comprising acts of

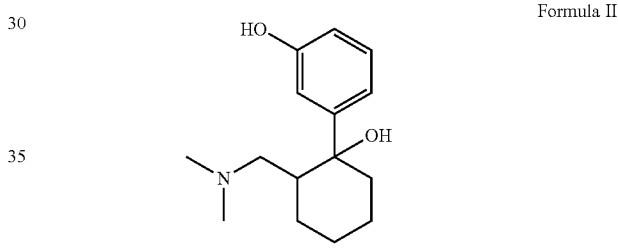

Formula II i) reacting tramadolof formula (I)

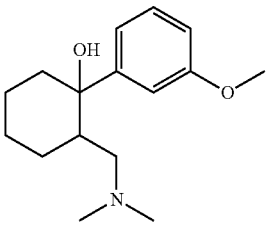

(Formula I)

with a potassium salt, in an organic solvent to obtain a mixture;
ii) heating the mixture;
iii) diluting the mixture with water to obtain an aqueous phase; and
iv) acidifying the aqueous phase with an acidic reagent and filtering to obtain compound of formula (II).

In an embodiment of the present invention, the potassium salt is selected from a group comprising potassium hydroxide and potassium t-butoxide.

In another embodiment of the present invention, the organic solvent is alcoholic solvent selected from group comprising polyethylene glycol, monoethyleneglycol and mixture thereof.

In still another embodiment of the present invention, the mixture is heated to a temperature ranging from about 190° C. to about 220° C.

In yet another embodiment of the present invention, acidifying the aqueous phase comprises adjusting the pH between 3 to 5 preferably 4, with a reagent selected from a group comprising an acidic reagent selected from a group comprising hydrochloric acid, phosphoric acid, acetic acid.

In yet another embodiment of the present invention, the process provides yield ranging from 88-95%.

In yet another embodiment of the present invention, O-Desmethyl tramadol has a purity ranging from 99.0% to 99.99% as measured by HPLC method.

The present invention is also in relation to a process for obtaining salt of O-Desmethyl tramadol comprising acts of a) reacting Tramadol of formula (I) with potassium salt in an organic solvent to obtain a mixture;

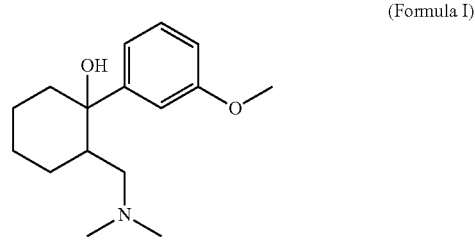 [SMILES: COc1cccc(C2(O)CCCCC2CN(C)C)c1]

(Formula I)

b) heating the mixture;

c) diluting the mixture with water to obtain an aqueous phase;

d) acidifying the aqueous phase with an acidic reagent and filtering to obtain 0-Desmethyltramadol of formula (II); and e) convertingthe O-Desmethyltramadol of formula (II) to salt of o-chlorobenzoic acid basifying with ammonia and treating with preferred acidic reagent to obtain salt of 0-De smethyltramadol.

In another embodiment of the present invention, the reagent is selected from a group comprising Hydrochloric acid, Succinic acid, Fumaric acid, Oxalic acid; preferably Hydrochloric acid to obtain hydrochloride salt of O-Desmethyltramadol.

In yet another embodiment of the present invention, salt of O-Desmethyltramadolis of purity ranging from 99.0% to 99.5% as measured by HPLC method.

The present invention is in relation to Demethylation of Tramadolto obtain 0-Desmethyltramadol, under alkaline conditions preferably in an alocoholic solvent in the presence of abase. The target compound obtained by the high yield (88-95%) process of the present invention has a purity of more than 85% as measured by HPLC. The process can be scaled up for industrial scale production as commercially available eco-friendly reagents are used in the reaction. Scheme 1, shows the process of the synthesis of Tramadol to 0-Desmethyl tramadol.

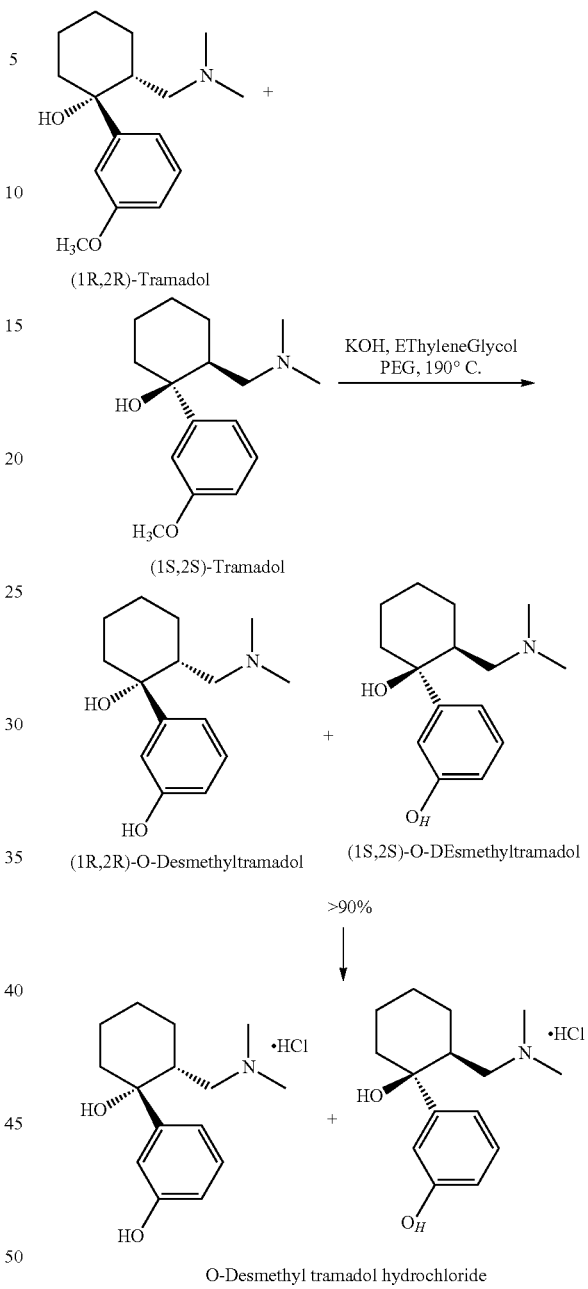

The base is selected from a group comprising potassium hydroxide, potassium t-butoxide; preferably potassium hydroxide. The alcoholic solvent is selected from a group comprising polyethylene glycol preferably polyethylene glycol 400, monoethylene glycol and mixture thereof.

Other solvents are selected from a group comprising dichloromethane, toluene, Xylene, dichloromethane, ethyl acetate.

The present invention helps in obtaining the salts of O-Desmethyltramadol, wherein the salts are of hydrochloric acid, succinic acid, fumaric acid; preferably hydrochloric acid.

The reaction involves heating Tramadol, in alcoholic solvent in presence of potassium hydroxide under phase transfer conditions to obtain O-Desmethyltramadol. The reaction proceeds in a facile manner to provide high yield (88-95%) of O-Desmethyl tramadol. FIG. 1 provides the HPLC diagram indicating the purity of O-Desmethyl Tramadol.

EXPERIMENTAL

The examples described below illustrates the process of synthesis of O-Desmethyltramadol however they do not limit the scope of the invention.

Example 1

To a clean flask, 125 g of commercially available Tramadol, (Cis-(1RS,2RS)-2-[(Dimethylamino)methyl]-1-(3-methoxyphenyl)cyclohexanol, 86% isomeric purity); 375 mL of ethylene glycol, 0.5 g of polyethylene glycol-400 and 175 g of Potassium hydroxide are added, under nitrogen atmosphere. Reaction mixture is then heated under nitrogen, by raising the temperature to about 195-200° C. over a period of about 3-4 h. The reaction mixture is maintained at the same temperature, for a period of 24 h. Later, the temperature of the reaction mixture is lowered to about 50° C., diluted with water and extracted with 1 lt of toluene. Toluene is concentrated in order to obtain unreacted Tramadol of about 5-10 g. Water layer is then acidified to pH 4 to get O-Desmethyltramadol, which is extracted with dichloromethane (500 mL×2 times). On concentration of dichloromethane layer, on drying the mixture at a temperature ranging from about 75° C. to about 80° C. for 8 hours O-Desmethyltramadol is obtained (95-100 g), about 85-86% isomeric purity by HPLC. This is converted to o-chlorobenzoic acid salt by dissolving in acetone and o-chloro benzoic acid (47 g). This salt has isomeric purity of about 94-96%. This is basified with ammonia and then converted to hydrochloride salt in acetone to get greater than 99% pure 0-Desmethyltramadol. FIG. 1 shows the HPLC diagram.

Example 2

To a clean flask, 1.25 kg of commercially available Tramadol (Cis-(1RS,2RS)-2-[(Dimethylamino)methyl]-1-(3-methoxyphenyl)cyclohexanol, isomeric purity>99%), 3.75 Lt of ethylene glycol, 0.5 kg of polyethylene glycol-400 and 1.75 kg of Potassium hydroxide are added, under nitrogen atmosphere. Reaction mixture is then heated under nitrogen, by raising the temperature to about 195-200° C. over a period of about 3-4 h. The reaction mixture is maintained at same temperature for a period of 24 h. The temperature of the reaction mixture is lowered to a temperature of about 50° C. and diluted with water and extracted with 5 Lt of toluene. Water layer is then acidified to pH 4 to get O-Desmethyltramadol, which is extracted with dichloromethane (2500 mL×2 times). On concentration of dichloromethane layer, on drying the mixture at a temperature ranging from about 75° C. to about 80° C. for 8 hours O-Desmethyltramadol of about 90% isomeric purity by HPLC is obtained (950-1100 g). This is converted to o-chlorobenzoic acid salt by dissolving in acetone and o-chloro benzoic acid (470 g). This salt had isomeric purity of about 94-96%. This is basified with ammonia, extracted in dichloromethane and concentrated. The residue thus obtained is dissolved in methanol (3.5 Lt), charcolized and filtered through high flow bed. Treated with IPA-HCL till pH 2 is achieved. Methanol is almost removed under vacuum and O-Desmethyltramadol is precipitated with 4 Lt of acetone. The product thus obtained is filtered and analysed by HPLC (>99) to get about 450-475 g pure O-Desmethyltramadol with isomeric purity of greater than 99%.

Example 3

Figure 2:
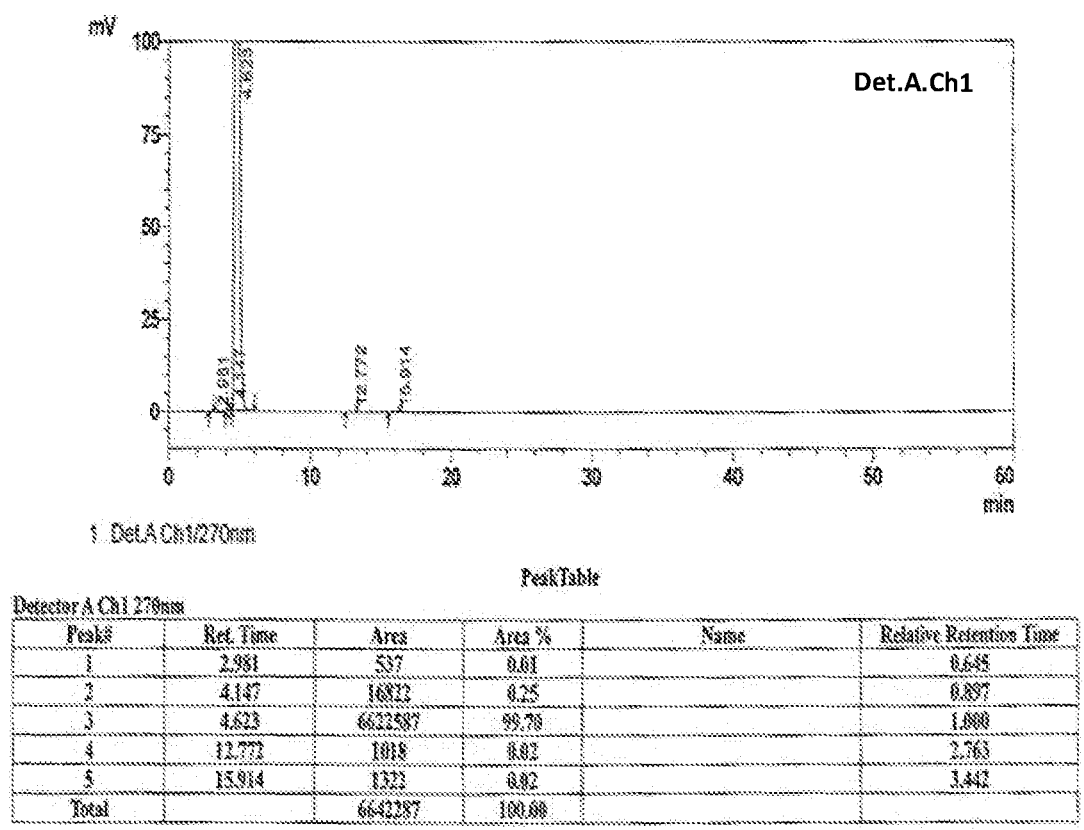
FIG. 2: HPLC diagram indicating the purity level of the 0-Desmethyl Tramadol (trans isomer)

The reaction procedure adopted in example 1 and 2 is applied to trans isomer-(RR,SS) of tramadol to gives the compound in similar yield and quality. Retention time of this isomer is at 4.6 min (FIG. 2). Tramadol BP-HPLC method is used.

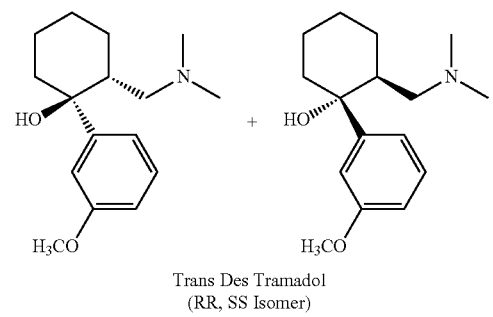 [SMILES: COc1cccc([C@]2(O)CCCC[C@@H]2CN(C)C)c1 ; COc1cccc([C@@]2(O)CCCC[C@H]2CN(C)C)c1]

Trans Des Tramadol
(RR, SS Isomer)

The present invention thus describes an eco-friendly, economical process for synthesis O-Desmethyltramadol,2-[(Dimethylamino)methyl]-1-(3-hydroxy phenyl)cyclohexanol). The process makes use of commercially available reagents. The compound has a purity of >99% measured by HPLC. The invention also provides facile method for the synthesis of salts, hydrochloride salt of 1-[2-(Dimethylamino)-1-(4-hydroxyphenyl)ethyl]-cyclohexanol. The simplicity of the process helps in easy scale up for industrial production.

The aforesaid description is enabled to capture the nature of the invention. It is to be noted however that the aforesaid description and the appended figures illustrate only a typical embodiment of the invention and therefore not to be considered limiting of its scope for the invention may admit other equally effective embodiments. It is an object of the appended claims to cover all such variations and modifications as can come within the true spirit and scope of the invention.

We claim:

1. A process for preparation of O-Desmethyl tramadol (formula (II)), comprising acts of

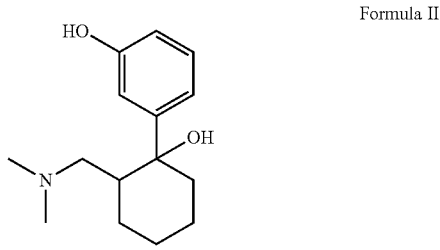 [SMILES: CN(C)CC1CCCCC1(O)c1cccc(O)c1]

Formula II i) reacting tramadol of formula (I)

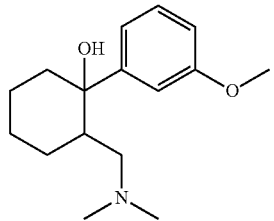
(Formula I)

with a potassium salt, in an organic solvent to obtain a mixture;
ii) heating the mixture;
iii) diluting the mixture with water to obtain an aqueous phase; and
iv) acidifying the aqueous phase with an acidic reagent and filtering to obtain compound of formula (II).

2. The process as claimed in claim 1, wherein the potassium salt is selected from a group comprising potassium hydroxide and potassium t-butoxide.

3. The process as claimed in claim 1, wherein the organic solvent is alcoholic solvent selected from group comprising polyethylene glycol, monoethyleneglycol and mixture thereof.

4. The process as claimed in claim 1, wherein the mixture is heated to a temperature ranging from about 190° C. to about 220° C.

5. The process as claimed in claim 1, wherein acidifying the aqueous phase comprises adjusting the pH between 3 to 5, with a reagent selected from a group comprising an acidic reagent selected from a group comprising hydrochloric acid, phosphoric acid, acetic acid.

6. The process as claimed in claim 1, wherein the process provides yield ranging from 88-95%.

7. The process as claimed in claim 1, wherein O-Desmethyl tramadol has a purity ranging from 99.0% to 99.99% as measured by HPLC method.

8. A process for obtaining salt of O-Desmethyl tramadol comprising acts of
   a) reacting Tramadol of formula (I) with potassium salt in an organic solvent to obtain a mixture;

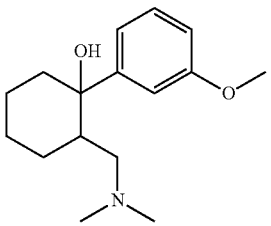
(Formula I)

b) heating the mixture;
   c) diluting the mixture with water to obtain an aqueous phase;
   d) acidifying the aqueous phase with an acidic reagent and filtering to obtain O-Desmethyltramadol of formula (II); and
   e) converting the O-Desmethyltramadol of formula (II) to salt of o-chlorobenzoic acid basifying with ammonia and treating with preferred acidic reagent to obtain salt of O-Desmethyltramadol.

9. The process as claimed in claim 8, wherein the reagent is selected from a group comprising Hydrochloric acid, Succinic acid, Fumaric acid, Oxalic acid to obtain hydrochloride salt of O-Desmethyltramadol.

10. The process as claimed in claim 8, wherein salt of O-Desmethyltramadol is of purity ranging from 99.0% to 99.5% as measured by HPLC method.

11. The process as claimed in claim 9, wherein salt of 0-Desmethyltramadol is of purity ranging from 99.0% to 99.5% as measured by HPLC method.

\* \* \* \* \*